(12) United States Patent
Krackow

(10) Patent No.: US 7,032,752 B2
(45) Date of Patent: Apr. 25, 2006

(54) CONTAINER AND METHOD FOR ENSURING THE PROVISION OF PROPER MEDICAL PROCEDURES

(76) Inventor: Kenneth A. Krackow, 58 N. Woodside La., Williamsville, NY (US) 14221

( * ) Notice: Subject to any disclaimer, the term of this patent is extended or adjusted under 35 U.S.C. 154(b) by 0 days.

(21) Appl. No.: 10/638,245

(22) Filed: Aug. 8, 2003

(65) Prior Publication Data

US 2005/0029145 A1    Feb. 10, 2005

(51) Int. Cl.
  *B65D 85/00* (2006.01)
  *A61B 19/02* (2006.01)
(52) U.S. Cl. ............... 206/438; 206/363; 206/459.5
(58) Field of Classification Search ............ 206/363, 206/364, 370, 438, 459.5, 534, 570
  See application file for complete search history.

(56) References Cited

U.S. PATENT DOCUMENTS

| | | | | |
|---|---|---|---|---|
| 3,497,982 A * | 3/1970 | Schulz | ................. | 40/312 |
| 3,679,047 A * | 7/1972 | Papirnyik | ................. | 206/39.5 |
| 3,826,421 A * | 7/1974 | Morse et al. | ............ | 229/123.1 |
| 5,366,087 A * | 11/1994 | Bane | ................. | 206/459.5 |
| D374,282 S * | 10/1996 | Hoftman | ................. | D24/130 |
| 5,866,181 A * | 2/1999 | Hill | ................. | 426/107 |
| 6,158,437 A * | 12/2000 | Vagley | ................. | 128/898 |
| 6,343,695 B1 * | 2/2002 | Petrick et al. | ............ | 206/534 |
| 6,398,028 B1 * | 6/2002 | Stovall | ................. | 206/390 |
| 6,564,945 B1 * | 5/2003 | Weinstein et al. | ......... | 206/531 |

* cited by examiner

*Primary Examiner*—John A. Ricci
(74) *Attorney, Agent, or Firm*—Phillips Lytle LLP

(57) ABSTRACT

The present invention provides a container (10) for medical instruments, packaging system and method for use by a medical provider in connection with a medical procedure such as surgery. The container includes a first container portion (12) adapted to contain medical instruments and a second container portion (14) configured to attach to the first container portion, with fasteners (16, 18, 20, 22) attached between the first and second container portions which are associated with reminder indicia (e.g., 17A, 19B, 21A, 23B). Among other things, the container is designed to ensure the provision of an appropriate medical procedure on the proper patient at the proper site.

21 Claims, 3 Drawing Sheets

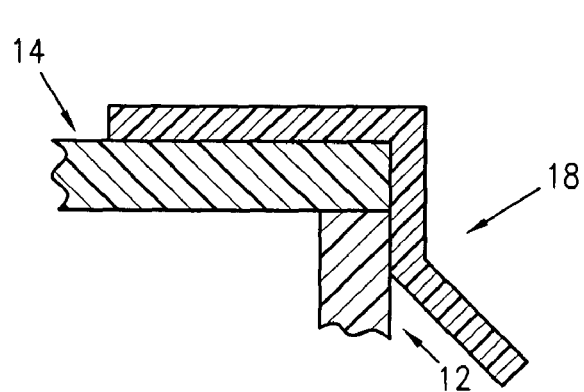
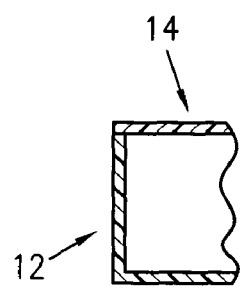
FIG. 5  FIG. 6
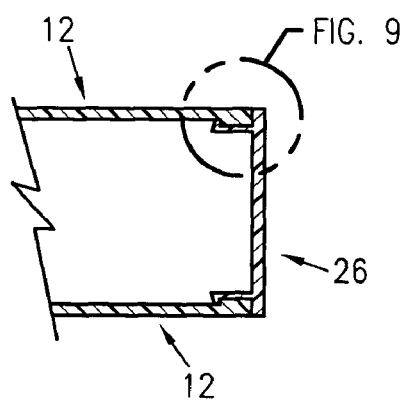
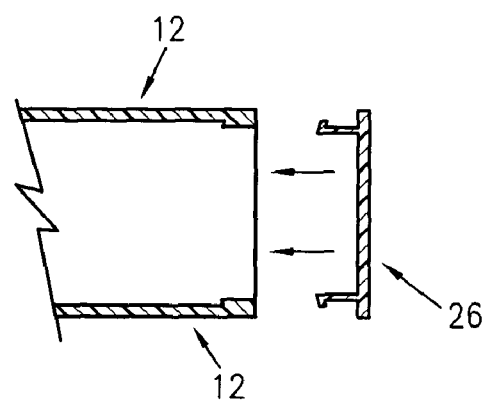
FIG. 7  FIG. 8
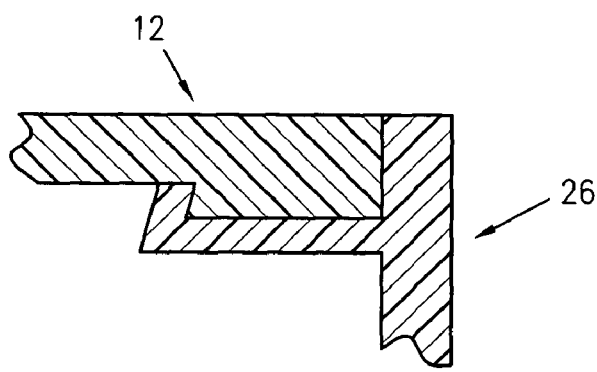
FIG. 9

CONTAINER AND METHOD FOR ENSURING THE PROVISION OF PROPER MEDICAL PROCEDURES

TECHNICAL FIELD

The present invention relates generally to medical, surgical and other healthcare procedures and instruments and, more particularly, to a device and a method for reliably and timely prompting a medical provider to verify patient identification, information and/or records relating to a patient or medical procedure prior to performing a medical procedure to prevent errors in such a procedure.

BACKGROUND ART

Medical instruments, devices and procedures are designed to save and improve the quality of life. When inappropriate surgeries or medical procedures are performed, however, or surgeries or procedures are performed on the wrong patient, at the wrong site, with the wrong medical instrument or working from improper information, a medical provider fails to furnish the patient with appropriate care. And, in the most unfortunate cases, injury or death may result.

Hundreds of injuries and deaths are caused each year by preventable errors and omissions, which errors may relate to "wrong-patient," "wrong-side," "wrong-site," "wrong-procedure," etc. events in the practice of medicine and surgery. Many of these incidents are caused by the performance of inappropriate medical procedures or the use of unsuitable medical instruments. For example, surgeries have been performed on the wrong patient or the wrong side of a patient; improper tests have been administered and improper examinations undertaken; x-rays have been taken of the wrong patient; procedures performed on the wrong joints; intravenous or inter-arterial lines have been placed in the right patient in the wrong location or site, etc.

Many electronic and other devices have been designed to ensure the safety of patients and reduce the risk of human error during medical procedures, but the potential for human error remains in many aspects of the provision of medical services. Moreover, a need exists for a device which provides a reminder or prompt contemporaneously or shortly before a medical procedure is undertaken. Also, a device is needed which alerts a surgeon or physician to patient and procedure information without the need for the surgeon or physician to rely heavily upon support personnel such as nurses, scrub technicians, or anesthesia personnel.

Medical instruments and devices are used in a variety of environments including operating rooms, hospital rooms, out-patient facilities and nursing homes. Errors and omissions may occur due to inattention, distractions from medical personnel, inadequate lighting, noise levels, and insufficient communication, for example, and from the design of medical instruments, the manner in which they are used or the procedures performed with them. Mistakes made in treatment of the wrong patient or site, for example, and implementation of the wrong medical procedures or instruments, not only hamper effective patient treatment and diagnosis, but in some cases can lead to injury or death.

The use of containers for medical instruments is well known in the prior art. For example, U.S. Pat. No. 5,641,065 (Owens) claims a medical instrument container for soaking, transport and storage of surgical instruments. U.S. Pat. No. 5,511,657 (Gnau) discloses a container for disposing of hazardous medical waste. U.S. Pat. No. 5,494,186 (Marsh) discloses a wall-mounted medical waste disposal container. Medical "reminder" devices are disclosed in U.S. Pat. No. 5,823,346 (Weiner), U.S. Pat. No. 6,441,722 (Weiner) and U.S. Pat. No. 6,449,218 (Lluch).

However, there exists a continuing need for containers and devices which enhance or ensure the health and safety of patients in hospitals, operating rooms, out-patient facilities, nursing homes, etc., and assist medical providers such as physicians, nurses, nurse practitioners, and their respective staffs and support personnel, in providing optimal medical services.

DISCLOSURE OF THE INVENTION

With parenthetical reference to the corresponding parts, portions or surfaces of the disclosed embodiment, merely for purposes of illustration and not by way of limitation, the present invention provides a container (10) for medical instruments, a packaging system and a method for use by a medical provider, such as a physician, nurse or nurse practitioner, in connection with a medical procedure such as surgery or other invasive procedures. As used herein, "medical instruments" and "medical devices" are equivalent.

The present invention alerts, prompts and/or reminds the medical provider to verify or check patient and procedure information such as the patient's name, the procedure, the history or planning of the procedure, the side and site(s) or location(s) where the procedure is to be performed, the specific details of the intended surgery or procedure, and other information, some of which is described more fully below. And, the arrangement and construction of such specific device, and other method-employing packaging not only prompts but, among other things, also physically impedes access to one or more implements, instruments, etc. necessary for beginning and performing the procedure or service. By such incorporation of a removable but nonetheless present, physical implement, the practitioner is necessarily reminded to check and verify the critical I.D. and other information necessary for addressing the problems of wrong-patient, wrong-side, wrong-site, etc. procedure performance.

In one aspect of the present invention, the container includes a first container portion (12) adapted to contain medical instruments such as sharps, scalpels (e.g. regular or long-handled scalpels), syringes, pins, needles, special trochars, or other invasive instruments (e.g., 30, 31, 32), a second container portion (14) configured to attach to the first container portion, and a fastener (16, 18, 20, 22) attached between the first and second container portions. The medical instrument may be the first implement of patient invasion to be used in connection with a particular surgery or procedure. The fastener is associated with reminder indicia relating to "patient information" including, but not limited to, "patient name," "patient ID," "patient data," "procedure," and "sides" and/or "sites" of the surgery or procedure to be performed (e.g., 17A, 17B, 19A, 19B, 21A, 21B). Other patient and/or procedure information may be significant in connection with certain procedures to ensure the overall purpose, correctness and safe performance of such procedures. The term fastener as used herein includes not only a breakable seal, breakaway tab, latch, adhesive strip or similar item, but any mechanism (such as a lock and key mechanism) whereby a medical provider must pause and/or take an additional action or step, or additional time, before performing a medical procedure while being alerted to, or prompted to check or verify, some relevant patient information and/or associated procedure-related information.

In another aspect of the invention, the fastener, first container portion and second container portion are configured and arranged such that the fastener must be disconnected in order for a medical provider to access the medical instrument(s) contained in the first container portion (and enclosed by the first and second container portions). In this aspect, the suitability of the medical instrument for use in connection with the relevant medical procedure may be ensured. Physicians and other medical personnel are alerted to or required to confirm patient information prior to commencement of a medical procedure.

In another aspect of the invention, the first container portion is transparent or translucent. In yet another aspect, the second container portion is transparent or translucent.

In another aspect of the present invention, a medical instrument (e.g., 30, 31, 32) is removably disposed in the container. In another aspect, the medical instrument is sterilized. In yet another aspect, the container itself is sterilized. In another aspect of the invention, the first container portion comprises an insertable side panel (26) whereby medical instruments may be placed in the first container portion prior to performing a medical procedure. In another aspect of the invention, the insertable side panel has flexible protrusions which engage two sides of the first container portion, thereby fully encapsulating the medical instrument prior to performance of the medical procedure or delivery to the appropriate medical provider. Thus, in this aspect, the medical instrument may only be accessed by removing or breaking the fastener(s).

In other aspects of the invention, reminder indicia are inscribed on the fastener. In other aspects, reminder indicia are inscribed on the first container portion and/or on the second container portion.

In another aspect, reminder indicia include a reference to patient information. In other aspects, the patient information comprises a patient name and/or identification (ID) number, medical procedure, site for a medical procedure, site upon which a medical procedure must be performed, patient history, laboratory results and/or radiographic results.

In other aspects, the fastener(s) comprise strip(s) of adhesive material. In other aspects, the fasteners comprise a plurality of strips of adhesive material which are associated with a corresponding plurality of reminder indicia. The fasteners may also be of a plastic or other material which is affixed to the first and/or second container portions. The invention also contemplates a second container portion with a lip, latch or flange, for example, which snaps into or otherwise attaches to the first container portion.

In other aspects, the medical instrument is a scalpel (regular or long-handled), biopsy trochar, syringe, needle, or other medical instrument.

Yet another aspect of the present invention provides a packaging system for a medical instrument for use by a medical provider in connection with a medical procedure wherein a fastener is configured to attach to the medical instrument, reminder indicia are inscribed on the fastener, and the fastener and reminder indicia are configured and arranged such that the reminder indicia are visible to the medical provider prior to a medical procedure. In this aspect, the invention may be applied to currently available medical devices or instruments which could be opened or accessed only after the fasteners were removed. In another aspect, the packaging system includes a container adapted to contain the medical instrument. In other aspects, the packaging system includes reminder indicia such as a reference to patient information, patient name, medical procedure, site or sites for a medical procedure, laboratory results and/or radiographic results.

Another aspect of the present invention is a packaging system for a medical instrument for use by a medical provider in connection with a medical procedure on a patient. In this aspect, the invention provides a means for communicating information associated with a patient to the medical provider and means for limiting access to the medical instrument by the medical provider, wherein the means for communicating information and the means for limiting access are configured and arranged such that the medical provider may access the medical instrument after the information associated with the patient is communicated to the medical provider. This aspect of the invention ensures the provision of appropriate medical procedures upon the proper patient and the suitability of the medical instrument for use in the related medical procedure. In another aspect, the packaging system includes a container adapted to contain the medical instrument. In yet another aspect, the means for communicating the information include a fastener inscribed with reference to patient information.

Another aspect of the invention provides a method for alerting a medical provider to information associated with a patient or medical procedure prior to performing said medical procedure. In this aspect, the invention contemplates the use of a container adapted to contain the medical instrument and the attachment of a fastener to the container, which fastener is associated with reminder indicia. In this aspect, the fastener limits access to the medical instrument prior to the medical procedure and the reminder indicia are communicated to the medical provider prior to the medical procedure. In another aspect of the invention, the method includes the added step of reviewing the reminder indicia. In yet another aspect, the method includes the further step of detaching the fastener.

In another aspect of the invention, the reminder indicia comprise patient information. In yet another aspect, the method includes the further step of verifying a patient name associated with the reminder indicia. In another aspect, the method includes the further step of verifying the medical procedure or verifying a site for the medical procedure.

The general object of the invention is to ensure the safety of a patient during a medical procedure.

Another significant object of the present invention is to ensure the safe and efficient use of medical instruments. Another object is to ensure that a medical provider undertakes the proper procedure, on the proper side, at the proper site, on the proper patient and/or with the proper medical instrument.

Yet another object is to alert a physician or other medical provider to relevant patient information, patient history and diagnosis information before performing a medical procedure. Another object is to provide such information passively and contemporaneously or shortly before the commencement of a surgery or medical procedure, and to reduce a medical provider's reliance on supporting personnel, or confirm the information provided by such personnel.

Still another object is to provide a physician or other medical provider with relevant clinical information for use in connection with a medical procedure, such as laboratory results, radiographic results, information displayed for review during a medical procedure, the location of the surgery and/or the medical procedure planned or contemplated.

Another object of the present invention is to ensure that a physician or other medical provider selects a suitable medical instrument for use in connection with a medical procedure. Yet another object is to provide a relatively inexpensive means for ensuring the use of appropriate medical equipment.

These and other objects and advantages will become apparent from the foregoing and ongoing written specification, the accompanying drawings and the appended claims.

BRIEF DESCRIPTION OF THE DRAWINGS

FIG. 5 is a side view of a fastener attached to the top portion and bottom portion of the medical container.

FIG. 6 is a side view of the medical container.

FIG. 7 is a top view of the medical container illustrating the insertable side panel.

FIG. 8 is a top view of the medical container illustrating the insertable side panel prior to insertion.

FIG. 9 is a top view of one corner of the medical container illustrating the engagement of the insertable side panel.

DESCRIPTION OF THE PREFERRED EMBODIMENTS

Figure 1:
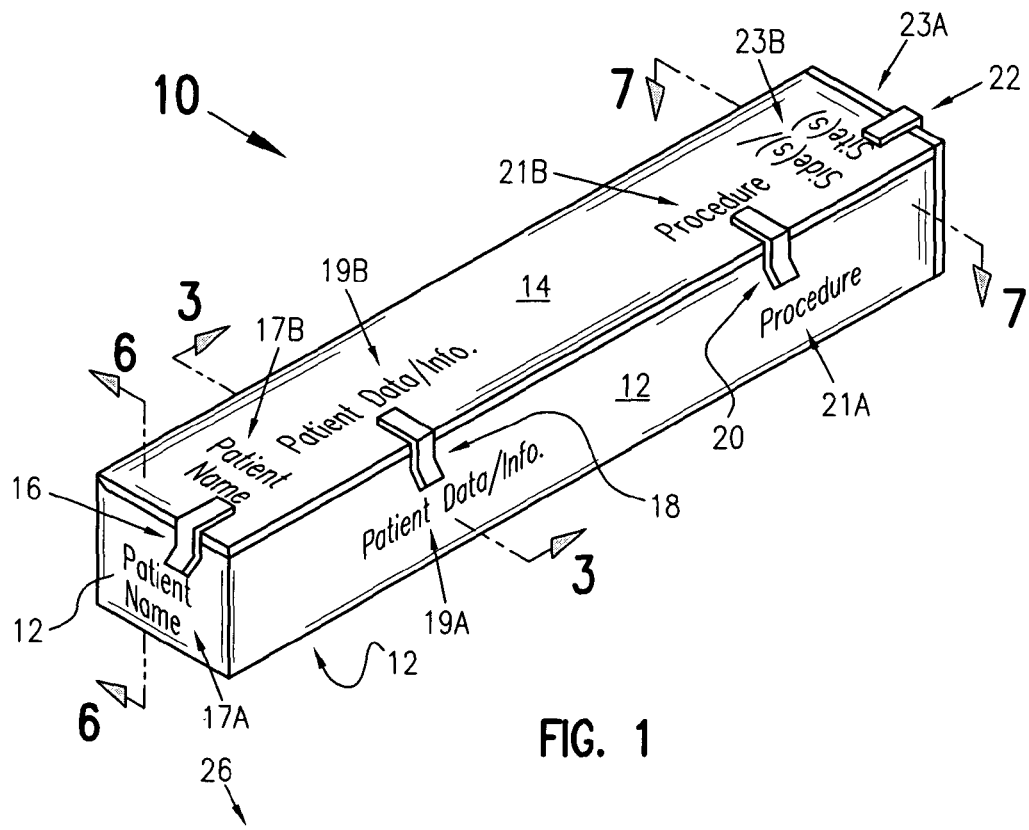
FIG. 1 is a perspective view of the medical container.

At the outset, it should be clearly understood that like reference numerals are intended to identify the same structural elements, parts, portions or surfaces consistently throughout the several drawing figures, as such elements, parts, portions or surfaces may be further described or explained by the entire written specifications, of which this detailed description is an integral part. Unless otherwise indicated, the drawings are intended to be read together with the specification, and are to be considered a portion of the entire written description of this invention. As used in the following description, the terms "horizontal," "vertical," "left," "right," "up" and "down," as well as adjectival and adverbial derivatives thereof(e.g., "horizontally," "rightwardly," "upwardly," "radially," etc.), simply refer to the orientation of the illustrated structure as the particular drawing figure faces the reader. Similarly, the terms "inwardly," "outwardly" and "radially" generally refer to the orientation of a surface relative to its axis of elongation, or axis of rotation, as appropriate.

Referring now to the drawings, the present invention provides an improved container for medical instruments, of which a first embodiment is generally indicated in FIG. 1. In FIG. 1, the container 10 is shown as having a series of fasteners, tabs or seals 16, 18, 20, 22 associated with corresponding reminder indicia 17A, 17B, 19A, 19B, 21A, 21B, 23A, 23B. FIG. 1 illustrates the first, or bottom, container portion 12 with inscribed reminder indicia 17A, 19A, 21A, 23A, and a second, or top, container portion 14 inscribed with corresponding reminder indicia 17B, 19B, 21B, 23B. The reminder indicia in the preferred embodiment are references to, for example, "patient name," "side(s)/site (s)," "patient ID," or "medical procedure." Such reminder indicia alert, remind or prompt the medical provider to verify or check such information prior to performing a procedure and before using the medical instrument.

Figure 10:
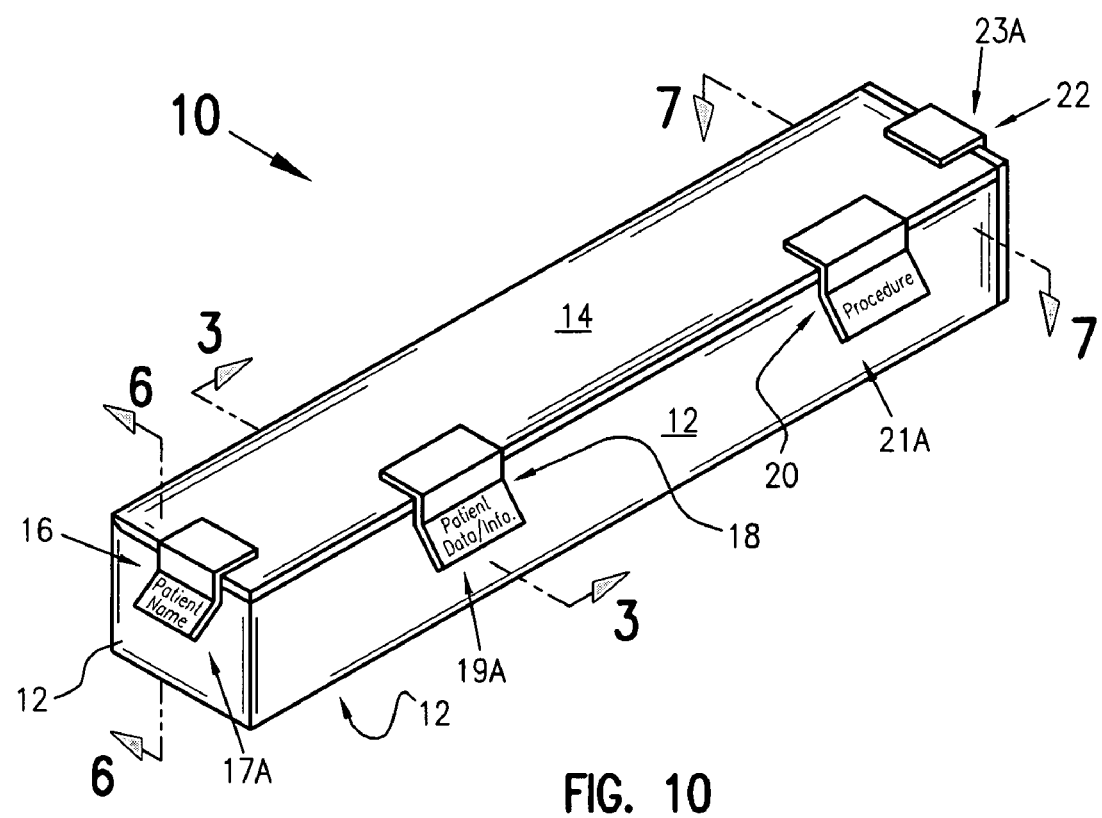
FIG. 10 is a perspective view of the medical container.

FIG. 10 illustrates the above-described features of FIG. 1 with reminder indicia 17A, 19A, 21A inscribed on fasteners 16, 18, 20.

Figure 3:
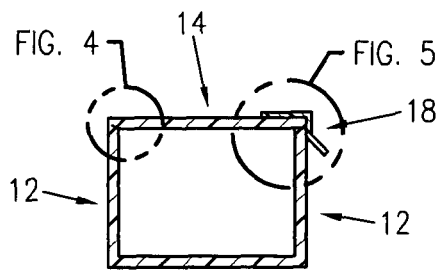
FIG. 3 is a side view of the medical container.
Figure 4:
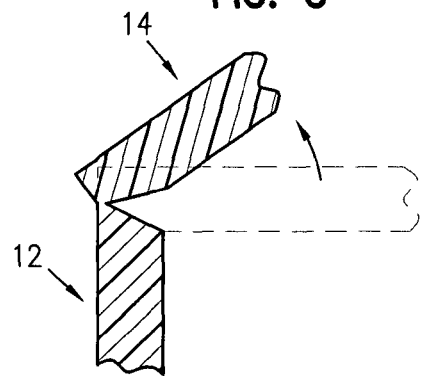
FIG. 4 is a side view of the hinge section of the medical container.

In this preferred embodiment, the second container portion 14 is a hinged lid which is attached to the first container portion by the fasteners 16, 18, 20, 22. FIGS. 3, 4 and 5 demonstrate the hinge between the first and second container portions, and the fastener as applied to the first and second container portions. Many other types of hinges and configurations may be used.

Figure 2:
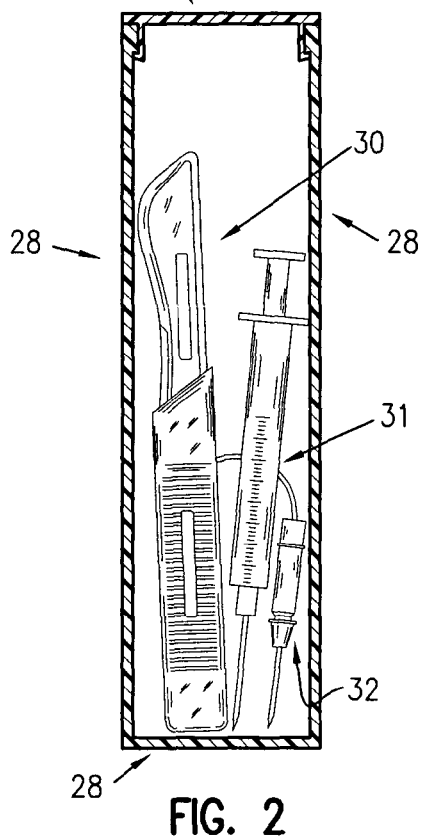
FIG. 2 is a top view of the medical container containing example medical instruments.

In a preferred embodiment, the medical instruments 30, 31, 32 are removably disposed in the medical container, as shown in FIG. 2. FIG. 2 also illustrates an insertable side panel 26 of a preferred embodiment of the invention. The insertable side panel is also illustrated in FIGS. 7, 8 and 9. In this embodiment, an insertable side panel includes two flexible protrusions which engage with two sides of the first container portion 12 to encapsulate the medical instruments. In this embodiment, it is contemplated that personnel in a supply department of a hospital or other medical facility could encapsulate or box the required medical instruments prior to surgery by inserting such medical instruments in the open end of a three-sided first container portion 28, and then inserting an insertable side panel 26 in the area defined by the open side of the first container portion. Thus, the support personnel, generally separate from the physician or other medical provider, could insert the insertable side panel such that it could not be removed unless the fasteners (e.g. breakable seals, tabs or adhesive strips) were disengaged and the second container portion separated from the first container portion. Other embodiments require the use of a lock and key mechanism, for example.

While there has been described what is believed to be the preferred embodiment of the present invention, those skilled in the art will recognize that other and further changes and modifications may be made thereto without departing from the spirit of the invention. Therefore, the invention is not limited to the specific details and representative embodiments shown and described herein. In the following claims, preamble language that is not specifically referred to in the body of a particular claim is to be construed as a mere statement of intended use and not as a limitation. Accordingly, various modifications may be made without departing from the spirit or scope of the general inventive concept as defined and differentiated by the following claims.

What is claimed is:

1. A container for a medical instrument for use by a medical provider in connection with a medical procedure, comprising:
   a first container portion adapted to contain said medical instrument;
   a second container portion configured to attach to said first container portion;
   a fastener attached between said first container portion and said second container portion, said fastener being associated with reminder indicia, wherein said reminder indicia are inscribed on said first container portion;
   said fastener, first container portion and second container portion being configured and arranged such that said fastener must be disconnected in order for said medical provider to access said medical instrument, thereby alerting said medical provider to said reminder indicia.

2. The container of claim 1 wherein said medical instrument is removably disposed in said container.

3. The container of claim 1 wherein said fastener comprises a strip of adhesive material.

4. The container of claim 1 wherein said fastener comprises a plurality of strips of adhesive material, said plurality of strips of adhesive material being associated with a corresponding plurality of reminder indicia.

5. A container for a medical instrument for use by a medical provider in connection with a medical procedure, comprising:
- a first container portion adapted to contain said medical instrument;
- a second container portion configured to attach to said first container portion;
- a fastener attached between said first container portion and said second container portion, said fastener being associated with reminder indicia, wherein said reminder indicia are inscribed on said second container portion;
- said fastener, first container portion and second container portion being configured and arranged such that said fastener must be disconnected in order for said medical provider to access said medical instrument, thereby alerting said medical provider to said reminder indicia.

6. The container of claim 2 wherein said medical instrument is removably disposed in said container.

7. The container of claim 5 wherein said fastener comprises a strip of adhesive material.

8. The container of claim 5 wherein said fastener comprises a plurality of strips of adhesive material, said plurality of strips of adhesive material being associated with a corresponding plurality of reminder indicia.

9. A container for a medical instrument for use by a medical provider in connection with a medical procedure, comprising:
- a first container portion adapted to contain said medical instrument, wherein said first container portion comprises an insertable side panel;
- a second container portion configured to attach to said first container portion;
- a fastener attached between said first container portion and said second container portion, said fastener being associated with reminder indicia;
- said fastener, first container portion and second container portion being configured and arranged such that said fastener must be disconnected in order for said medical provider to access said medical instrument, thereby alerting said medical provider to said reminder indicia.

10. The container of claim 9 wherein said insertable side panel comprises one or more protrusions capable of engagement with said first container portion.

11. The container of claim 9 wherein said medical instrument is removably disposed in said container.

12. The container of claim 9 wherein said fastener comprises a strip of adhesive material.

13. The container of claim 9 wherein said fastener comprises a plurality of strips of adhesive material, said plurality of strips of adhesive material being associated with a corresponding plurality of reminder indicia.

14. A packaging system for a medical instrument for use by a medical provider in connection with a medical procedure on a patient, comprising:
- means for communicating information associated with said patient to said medical provider, wherein said means for communicating information comprises an inscription on said container;
- means for limiting access to said medical instrument by said medical provider;
- a container adapted to contain said medical instrument;
- wherein said means for communicating information and said means for limiting access are configured and arranged such that said medical provider may access said medical instrument after said information associated with said patient is communicated to said medical provider, thereby alerting said medical provider to verify said information.

15. The packaging system of claim 14 wherein said means for communicating said information comprises a fastener, said fastener being inscribed with a reference to said information.

16. The packaging system of claim 14 wherein said information associated with said patient comprises a patient name.

17. The packaging system of claim 14 wherein said information associated with said patient comprises a medical procedure.

18. The packaging system of claim 14 wherein said information associated with said patient comprises a site for said medical procedure.

19. The packaging system of claim 14 wherein said information associated with said patient comprises a site for patient history.

20. The packaging system of claim 14 wherein said information associated with said patient comprises a site for laboratory results.

21. The packaging system of claim 14 wherein said information associated with said patient comprises a site for radiographic results.

* * * * *